(12) United States Patent
Okui et al.

(10) Patent No.: US 7,436,516 B2
(45) Date of Patent: Oct. 14, 2008

(54) REFLECTION CHARACTERISTIC MEASURING APPARATUS

(75) Inventors: Yoshihiro Okui, Daito (JP); Jun Matsumoto, Sakai (JP); Kenji Imura, Toyohashi (JP)

(73) Assignee: Konica Minolta Sensing, Inc., Sakai-Shi (JP)

( * ) Notice: Subject to any disclaimer, the term of this patent is extended or adjusted under 35 U.S.C. 154(b) by 74 days.

(21) Appl. No.: 11/708,221

(22) Filed: Feb. 19, 2007

(65) Prior Publication Data

US 2007/0195327 A1  Aug. 23, 2007

(30) Foreign Application Priority Data

Feb. 22, 2006  (JP) .............................. 2006-045514

(51) Int. Cl.
*G01N 21/55* (2006.01)
(52) U.S. Cl. ..................... 356/445; 356/446; 356/402
(58) Field of Classification Search ......... 356/445–446, 356/402, 600–606; 250/228; 39/112.09
See application file for complete search history.

(56) References Cited

U.S. PATENT DOCUMENTS

| | | | | |
|---|---|---|---|---|
| 5,018,127 A | * | 5/1991 | Ando ..................... | 369/112.09 |
| 5,367,379 A | * | 11/1994 | Makino ..................... | 356/446 |
| 6,088,117 A | * | 7/2000 | Imura et al. ................. | 356/445 |
| 6,172,365 B1 | * | 1/2001 | Hiroi et al. .................. | 250/310 |
| 6,707,553 B1 | * | 3/2004 | Imura ......................... | 356/402 |
| 7,262,854 B2 | * | 8/2007 | Imura ......................... | 356/402 |
| 7,355,712 B2 | * | 4/2008 | Imura et al. ................. | 356/445 |

FOREIGN PATENT DOCUMENTS

| | | | | |
|---|---|---|---|---|
| JP | 61095793 A | * | 5/1986 | |
| JP | 03246452 A | * | 11/1991 | |
| JP | 3185031 B2 | | 5/2001 | |

* cited by examiner

*Primary Examiner*—Sang Nguyen
(74) *Attorney, Agent, or Firm*—Sidley Austin LLP

(57) ABSTRACT

A reflection characteristic measuring apparatus includes: a light irradiating member for irradiating light toward a sample surface to be measured; a light detector, having a two-dimensional light receiving surface, for receiving reflection light from the sample surface illuminated with the light irradiated by the light irradiating member to output two-dimensional light receiving data concerning a first area corresponding to an area of the light receiving surface; an area setter for setting a second area at an appropriate position within the first area, the second area being smaller than the first area, to restrict light receiving data to be used in obtaining a reflection characteristic of the sample surface; and a calculator for obtaining a characteristic of the sample surface, based on two-dimensional light receiving data concerning the second area. The area setter detects whether the two-dimensional light receiving data concerning the first area includes a peak value concerning light receiving; sets the second area, with a position of the peak value being defined as a reference position, if the peak value is detected; and sets the second area, with a central position on the first area being defined as the reference position, if the peak value is not detected.

9 Claims, 9 Drawing Sheets

REFLECTION CHARACTERISTIC MEASURING APPARATUS

This application is based on Japanese Patent Application No. 2006-45514 filed on Feb. 22, 2006, the contents of which are hereby incorporated by reference.

BACKGROUND OF THE INVENTION

1. Field of the Invention

The present invention relates to a reflection characteristic measuring apparatus for measuring the gloss of a sample surface.

2. Description of the Background Art

Conventionally, there is known a reflection characteristic measuring apparatus for measuring the gloss of a sample surface. FIG. 10 is a diagram showing a construction of a conventional reflection characteristic measuring apparatus 100. The reflection characteristic measuring apparatus 100 includes an incident-side optical system 101 and a reflection-side optical system 102. In the reflection characteristic measuring apparatus 100, light is irradiated toward a sample surface S from the incident-side optical system 101 disposed at a position with a certain angle with respect to the normal G passing a certain point on the sample surface S. Then, the reflection light from the sample surface S is incident to the reflection-side optical system 102 disposed at a position with a certain angle with respect to the normal G.

The incident-side optical system 101 and the reflection-side optical system 102 have diaphragms 103 and 104, respectively. The diaphragm 103 of the incident-side optical system 101 is adapted to direct the light from a light source 105 toward the sample surface S within a predetermined opening angle. The diaphragm 104 of the reflection-side optical system 102 is adapted to direct the reflection light from the sample surface S toward a light receiving surface of a light detector 106 within a predetermined light detection angle. The gloss of the sample surface S is measured, using an output from the light detector 106 which has received the thus-regulated reflection light.

Japanese Patent No. 3,185,031 discloses an arrangement concerning the aforementioned type of reflection characteristic measuring apparatus, wherein a line sensor is provided as a light detector for receiving reflection light from a sample surface to be measured so that specular reflection light from the sample surface forms a focal point on the line sensor. With use of the apparatus, the gloss of the sample surface is measured by detecting a light amount distribution concerning reflection light incident onto the line sensor.

In use of the reflection characteristic measuring apparatus shown in FIG. 10, as shown in FIG. 11, if the setting position of the sample surface S is tilted by the angle θ, the direction along which the reflection light from the sample surface S is incident to the reflection-side optical system is tilted by the angle 2θ with respect to the original condition before the tilting. In FIG. 11, the diaphragm 104 and the light detector 106 are not illustrated. In this condition, as shown in FIG. 12, assuming that the focal length of a lens element 107 of the reflection-side optical system 102 through which the reflection light is directed toward the light detector 106 is defined as f, the focusing position is displaced by f×tan 2θ on the focusing plane from the focusing position M of reflection light obtained in a condition that the sample surface S is not tilted.

In the conventional measuring apparatus 100, the dimensions of the aperture of the diaphragm 104 provided in the reflection-side optical system 102 are fixed. Accordingly, if the sample surface S is tilted as mentioned above, the amount of reflection light detected by the light detector 106 is varied with respect to a proper condition where the sample surface S is not tilted relative to the measuring apparatus 100. This results in failure of accurate detection of the gloss of the sample surface S.

Also, even if the sum of the amount of reflection light detected by the light detector 106 is identical concerning sample surfaces whose gloss is to be measured, the sample surfaces include sample surfaces having a relatively small ratio of specular reflection light component to diffusion light component as shown in FIG. 13A, and sample surfaces having a relatively large ratio of specular reflection light component to diffusion light component as shown in FIG. 13B. The curves (1) and (2) in FIGS. 13A and 13B show magnitudes of intensities of reflection light with respect to a distance from the reflection point Z. As is obvious from FIGS. 13A and 13B, the intensity of reflection light passing a relevant point on the curve (1), (2) is increased, as the distance from the reflection point Z to the point on the curve (1), (2) is increased.

In the conventional reflection characteristic measuring apparatus 100, the dimensions of the aperture of the diaphragm 104 provided in the reflection-side optical system 102 are fixed, and the gloss of the sample surface is measured based on the sum of light passing through the aperture. Accordingly, if the sum of the amount of reflection light detected by the light detector 106 is identical concerning the sample surfaces to be measured, all the sample surfaces are determined to have the same degree of gloss, which makes it impossible to distinguish the sample surfaces one from another. Even with use of the method disclosed in the above publication, the drawback cannot be overcome.

SUMMARY OF THE INVENTION

In view of the above problems residing in the conventional examples, it is an object of the present invention to provide a reflection characteristic measuring apparatus that enables to accurately measure the gloss of a sample surface to be measured.

According to an aspect of the invention, a reflection characteristic measuring apparatus includes: a light irradiating member for irradiating light toward a sample surface to be measured; a light detector, having a two-dimensional light receiving surface, for receiving reflection light from the sample surface illuminated with the light irradiated by the light irradiating member to output two-dimensional light receiving data concerning a first area corresponding to an area of the light receiving surface; an area setter for setting a second area at an appropriate position within the first area, the second area being smaller than the first area, to restrict light receiving data to be used in obtaining a reflection characteristic of the sample surface; and a calculator for obtaining a characteristic of the sample surface, based on two-dimensional light receiving data concerning the second area. The area setter detects whether the two-dimensional light receiving data concerning the first area includes a peak value concerning light receiving; sets the second area, with a position of the peak value being defined as a reference position, if the peak value is detected; and sets the second area, with a central position on the first area being defined as the reference position, if the peak value is not detected.

These and other objects, features and advantages of the present invention will become more apparent upon reading the following detailed description along with the accompanying drawing.

DETAILED DESCRIPTION OF THE PREFERRED EMBODIMENTS

Figure 1:
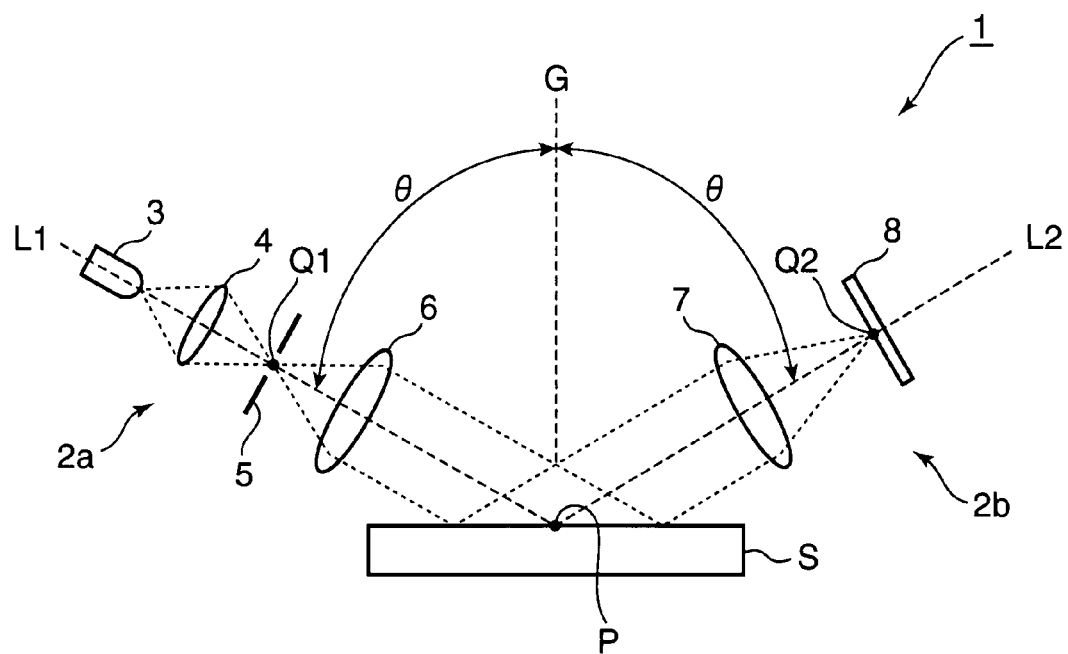
FIG. 1 is a diagram showing a reflection characteristic measuring apparatus according to an embodiment of the invention.

In the following, a reflection characteristic measuring apparatus embodying the invention is described referring to the drawings. FIG. 1 is a diagram showing the reflection characteristic measuring apparatus according to the embodiment of the invention.

As shown in FIG. 1, the reflection characteristic measuring apparatus 1 includes an incident-side optical system 2a, as a first optical system or a light irradiating member, for allowing light to be irradiated onto a predetermined area (hereinafter, called as "irradiation area") on a sample surface S to be measured; and a reflection-side optical system 2b, as a second optical system, for allowing reflection light from the irradiation area to be incident.

The incident-side optical system 2a and the reflection-side optical system 2b are disposed in respective positions opposed to each other with respect to the normal G of the sample surface S, wherein the normal G passes an intersection P of optical axes L1 and L2 of the optical systems 2a and 2b. The incident-side optical system 2a is disposed at such a position that its optical axis L1 defines an angle θ (θ is e.g. 60°, hereinafter, the angle θ is called as "incident angle θ") with respect to the normal G in a condition that the sample surface S is set in a proper position, in other words, is not tilted. The reflection-side optical system 2b is disposed at such a position that its optical axis L2 defines an angle θ (θ is e.g. 60°) with respect to the normal G. The incident angle θ is defined by ISO2813, ISO7668, JIS Z8741 or a like criterion, and may be e.g. 20° or 80°.

Throughout the specification, the expression "setting position of the sample surface is not changed" means that the sample surface is not tilted i.e. the sample surface is set in a proper position, and the expression "setting position of the sample surface is changed" means that the sample surface is tilted with respect to the proper position.

Reflection light includes a specular reflection light component whose angle (hereinafter, called as "reflection angle") with respect to the normal G is substantially the same or close to the incident angle θ, and a diffusion light component. Whereas a sample surface with more gloss has a larger ratio of specular reflection light component to diffusion light component, in other words, a smaller ratio of diffusion light component to specular reflection light component, a sample surface with less gloss has a larger ratio of diffusion light component, in other words, a smaller ratio of specular reflection light component. The reflection characteristic measuring apparatus 1 measures the gloss of the sample surface S i.e. the degree of reflection in the case where the sample surface is illuminated with light, based on the amount of reflection light composed of the specular reflection light component and the diffusion light component.

The incident-side optical system 2a includes, on the optical axis L1, a light source 3, a first lens element 4, a diaphragm 5, and a second lens element 6 in this order from the farthest position from the intersection P.

The light source 3 includes e.g. an LED, and outputs light toward the sample surface S to be measured. The first lens element 4 condenses light outputted from the light source 3. The diaphragm 5 is adapted to direct the light transmitted through the first lens element 4 toward the second lens element 6 within a predetermined angular range, and is disposed at a focal position of the second lens element 6. The second lens element 6 directs the light passing through the diaphragm 5 as substantially parallel light toward the sample surface S to be measured.

The reflection-side optical system 2b includes, on the optical axis L2, a third lens element 7, and an image sensor 8 as a light detector in this order from the nearest position from the intersection P. The third lens element 7 condenses reflection light from the sample surface S, and directs the reflection light toward the image sensor 8. Unlike the incident-side optical system 2a, the reflection-side optical system 2b is an optical system excluding a diaphragm.

Figure 2:
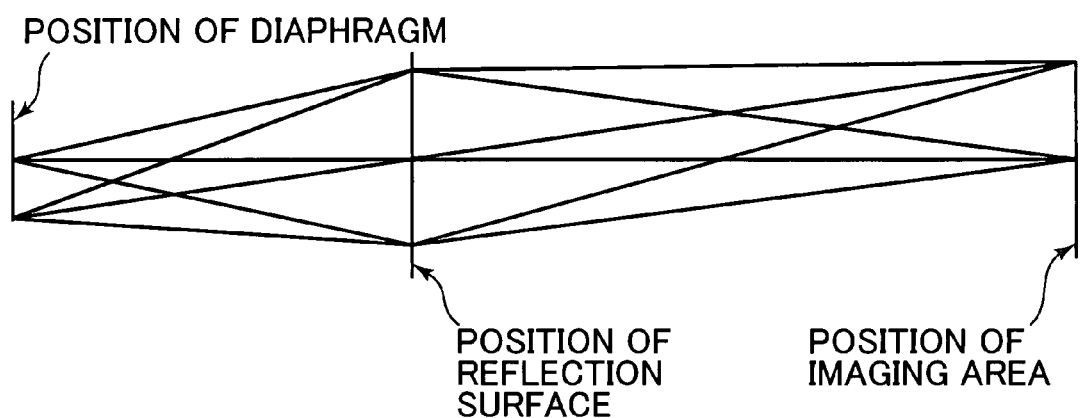
FIG. 2 is a diagram showing behaviors of light directed from a second lens element toward a sample surface to be measured, and of light directed from a third lens element toward an image sensor.

As illustrated in FIG. 2, concerning the incident-side optical system 2a and the reflection-side optical system 2b in the embodiment, the diaphragm 5 and an imaging area i.e. a light receiving surface of the image sensor 8 are positioned in optically conjugated relations with each other. The focal length of the third lens element 7 is defined so that the specular reflection light is incident within an area of the light receiving surface of the image sensor 8, as long as the sample surface S is set within a predetermined angular range.

The image sensor 8 is disposed at the focal position of the third lens element 7. The image sensor 8 is a CCD (Charge Coupled Device) area sensor, in which multitudes of photoelectric conversion elements (hereinafter, called as "pixels") constituted of e.g. photodiodes are two-dimensionally arranged in a matrix. The image sensor 8 converts a subject light image formed on the imaging area of the image sensor 8 into analog electric signals for output as pixel signals i.e. two-dimensional light receiving data. The image sensor 8 may include a CMOS image sensor, other than the CCD area sensor.

Figure 3:
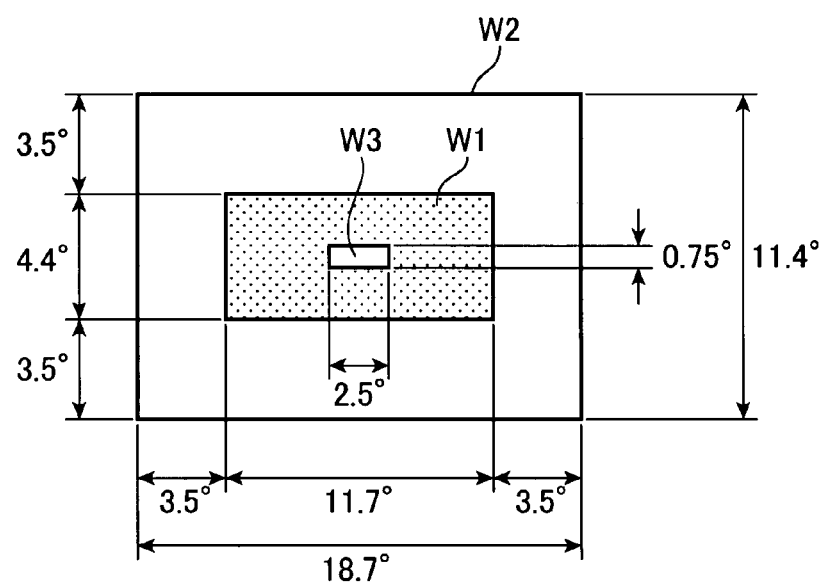
FIG. 3 is a diagram showing a relationship between an area W1 within which the light from the third lens element is irradiated onto a light receiving surface of the image sensor, and a light receiving area W2 of the image sensor.

The two-dimensional light receiving surface of the image sensor 8 has an area larger than a targeted pixel area where the gloss of the sample surface is to be calculated. Specifically, as shown in FIG. 3, assuming that the targeted pixel area of the image sensor 8 where the gloss is to be calculated based on the light directed from the third lens element 7 is defined as W1, the area W2 of the light receiving surface of the image sensor 8 i.e. the dimensions of the light receiving surface is defined as W2 (>W1). In the case where the sample surface S is set in a proper position, and the reflection light is parallel light, the light directed from the third lens element 7 is received on a central part of the light receiving surface of the image sensor 8. The area W3 shows the magnitude of light that is directed from the second lens element 6 toward the sample surface S, assuming that the sample surface S functions as a specular reflection surface i.e. a mirror surface.

Figure 4:
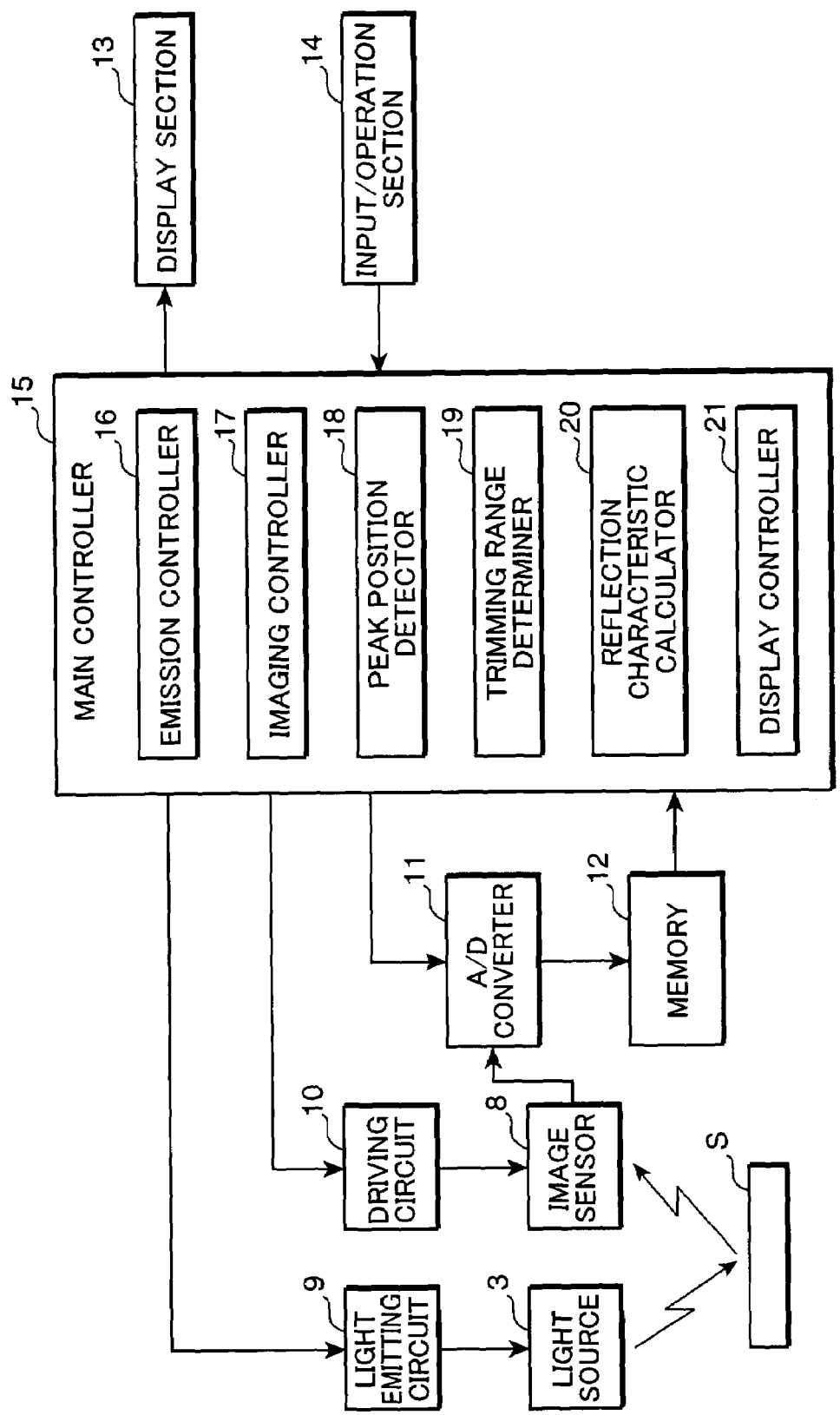
FIG. 4 is a block diagram showing an electrical configuration of the reflection characteristic measuring apparatus.

FIG. 4 is a block diagram showing an electrical configuration of the reflection characteristic measuring apparatus 1. As shown in FIG. 4, the reflection characteristic measuring apparatus 1 includes a light source 3, an image sensor 8, a light emitting circuit 9, a driving circuit 10, an A/D converter 11, a memory 12, a display section 13, an input/operation section 14, and a main controller 15.

The light source 3 and the image sensor 8 in FIG. 4 correspond to the light source 3 and the image sensor 8 shown in FIG. 1, respectively. The light emitting circuit 9 causes the light source 3 to emit light in accordance with a command signal from the main controller 15. The driving circuit 10 causes the image sensor 8 to perform an imaging operation in accordance with a command signal from the main controller 15.

The A/D converter 11 converts pixel signals outputted from the image sensor 8 into digital pixel signals (hereinafter, called as "pixel data") constituted of plural bits e.g. 10 bits. The memory 12 temporarily stores the pixel data outputted from the A/D converter 11, and is used as a working area in which the main controller 15 implements various processing with respect to the pixel data.

The display section 13 includes e.g. an LCD (Liquid Crystal-Display), and displays the degree of gloss of the sample surface S obtained by the main controller 15. The input/operation section 14 includes a power button for turning on and off a main power supply of the reflection characteristic measuring apparatus 1, and switches for allowing the user to enter designation to start gloss measurement concerning the sample surface S.

The main controller 15 includes a microcomputer built-in with a storage such as an ROM (Read Only Memory) in which a control program or the like is stored, or a flash memory for temporarily storing data. The main controller 15 functionally has an emission controller 16, an imaging controller 17, a peak position detector 18, a trimming range determiner 19, a reflection characteristic calculator 20, and a display controller 21 to control the aforementioned elements in association with each other.

The emission controller 16 controls an operation of the light emitting circuit 9. Upon receiving a designation to start gloss measurement concerning the sample surface S by way of the input/operation section 14, the emission controller 16 controls the light source 3 to emit light for a predetermined time duration.

The imaging controller 17 controls an operation of the driving circuit 10. Upon receiving a designation to start gloss measurement concerning the sample surface S by way of the input/operation section 14, the imaging controller 17 controls the image sensor 8 to perform an imaging operation.

The peak position detector 18 detects a targeted pixel (hereinafter, the position of the targeted pixel is called as "peak position") which outputs a maximal output value among output values of the pixels of the image sensor 8. As mentioned above, a sample surface with more gloss has a larger ratio of specular reflection light component to diffusion light component. Concerning a sample surface S with a relatively large degree of gloss, the output value (hereinafter, called as "peak value") of the pixel which has received the specular reflection light is relatively large, as compared with the output values of the other pixels.

Figure 5:
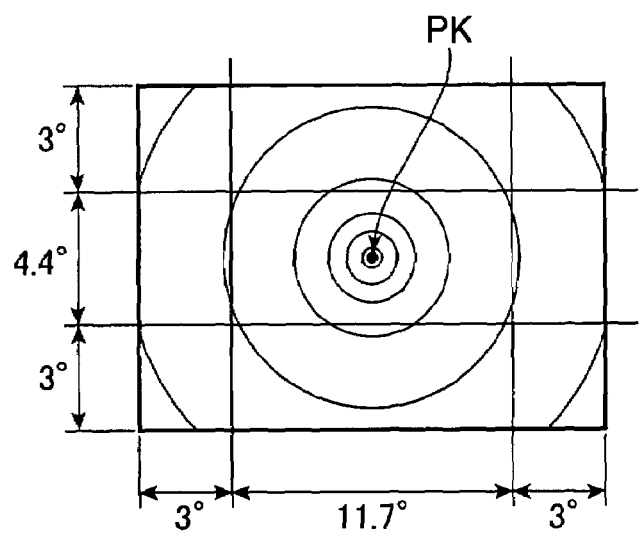
FIG. 5 is an explanatory diagram showing an intensity distribution on reflection light with a peak value, in the case where the setting position of a sample surface is not changed.

FIG. 5 is a diagram showing an intensity distribution on reflection light from the sample surface S having the peak value in the case where the setting position of the sample surface S is not changed. As shown in FIG. 5, in the case where the reflection light from the sample surface S has the peak value, the peak value appears at a certain position i.e. the peak position PK where the output value is significantly increased. Also, the output value of the pixel is decreased, as the distance from the peak position PK is increased. By connecting the pixels having substantially the same output values by a line, an output distribution profile is obtained, in which substantially concentric circles are depicted, with the peak position PK serving as the center of the circles.

On the other hand, concerning a sample surface S with a relatively small degree of gloss, the light received on the image sensor 8 includes a relatively large ratio of diffusion light component. Accordingly, the intensity distribution concerning the incident light on the light receiving surface of the image sensor 8 shows a moderate gradient, and the output values of the pixels of the image sensor 8 do not include the aforementioned peak value.

The peak position detector 18 detects whether the output distribution profile concerning the pixels includes a peak value. If it is detected that the output distribution profile includes the peak value, the peak position detector 18 judges the pixel which has outputted the peak value, as a pixel which has received the specular reflection light, and defines the position of the pixel as the peak position. If, on the other hand, it is detected that the output distribution profile does not include the peak value, the peak position detector 18 judges that the peak position does not exist concerning the light receiving data.

An example of the method for detecting whether the output distribution profile includes the peak value is a method in which a maximal output value among the pixel output values is defined as a peak value itself. Also, there is proposed a method comprising: comparing pixel output values one with another to detect a maximal output value so that the position of the pixel having the maximal output value is defined as a peak position PK; judging that there exists a peak value if a difference between the output value at the peak position PK and an output value of a pixel at a position adjacent the peak position PK is equal to or larger than a predetermined value; and judging that there does not exist a peak value if the difference is smaller than the predetermined value.

The trimming range determiner 19 corresponding to an area setter determines a predetermined range corresponding to a second area, whose area is smaller than the area corresponding to a first area of the light receiving surface of the image sensor 8, as a trimming range to restrict the light receiving data to be used in obtaining a reflection characteristic of the sample surface S i.e. calculating the degree of gloss in the embodiment.

Figure 6:
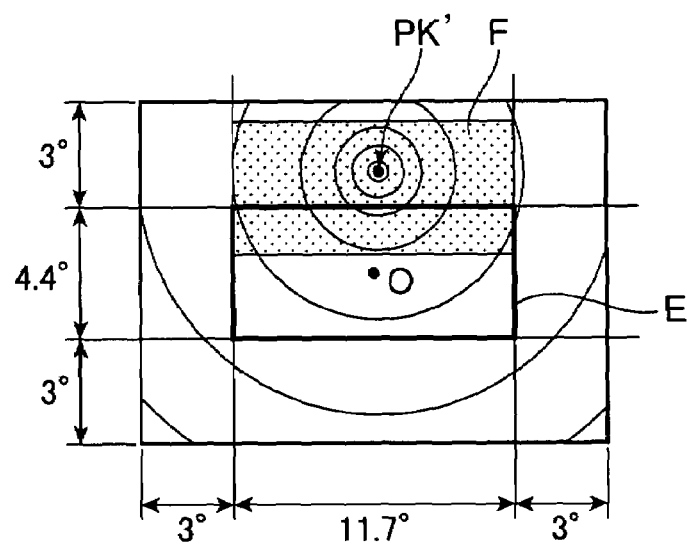
FIG. 6 is an explanatory diagram showing an intensity distribution on reflection light with a peak value, in the case where the setting position of the sample surface is changed.
Figure 10:
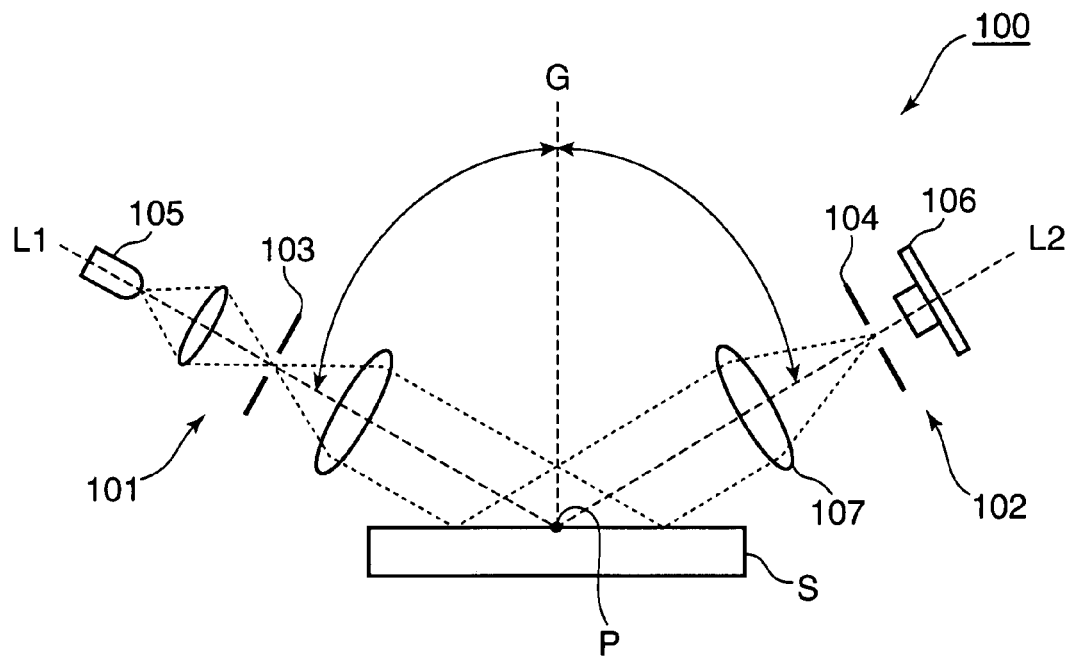
FIG. 10 is a diagram showing a reflection characteristic measuring apparatus according to a conventional art.
Figure 11:
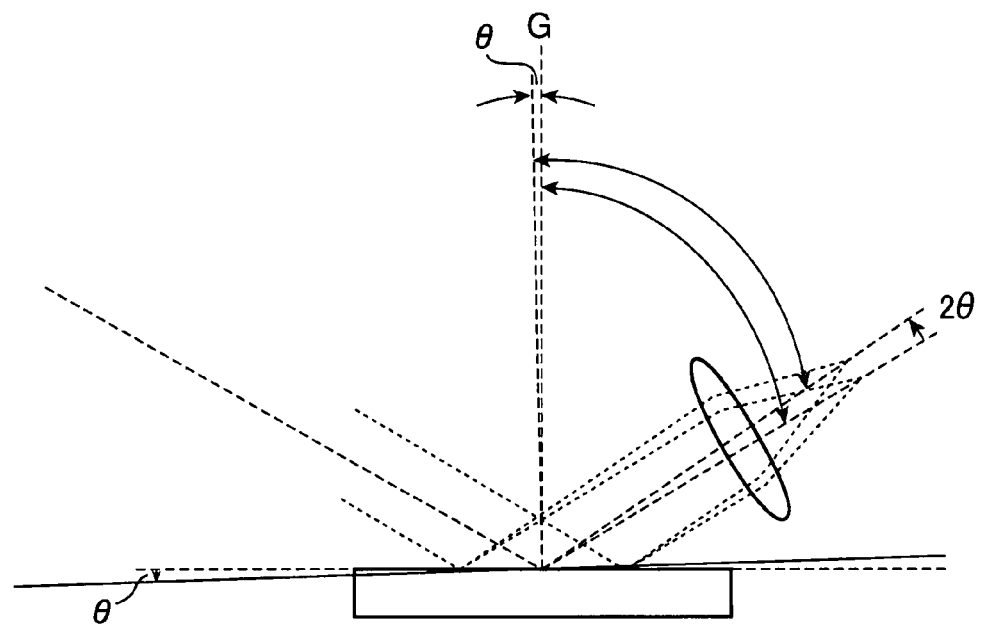
FIGS. 11, 12, 13A, and 13B are diagrams for describing drawbacks involved in the conventional art.
Figure 12:
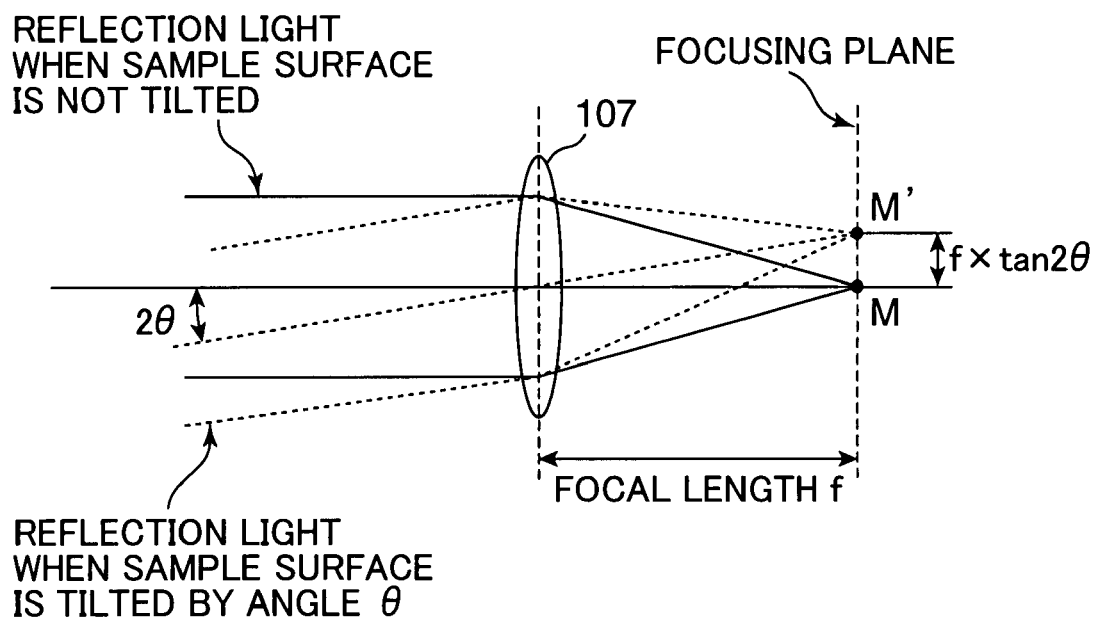
Figure 13A:
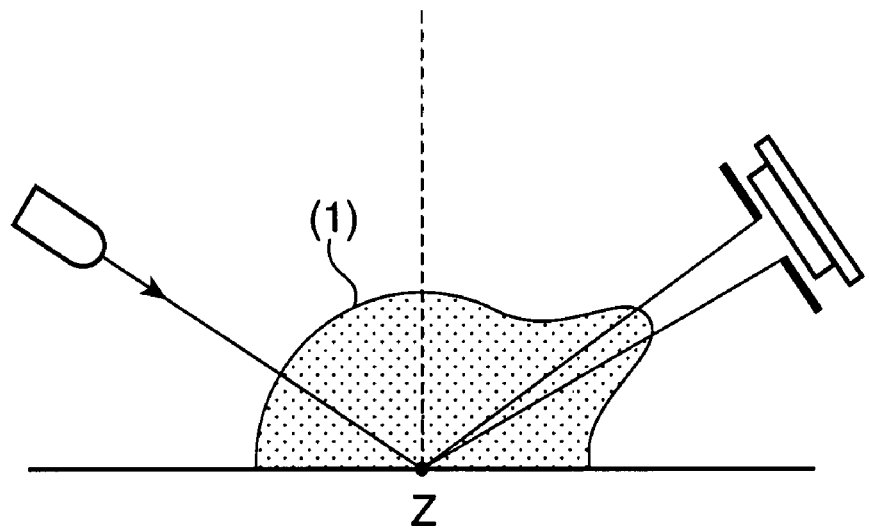
Figure 13B:
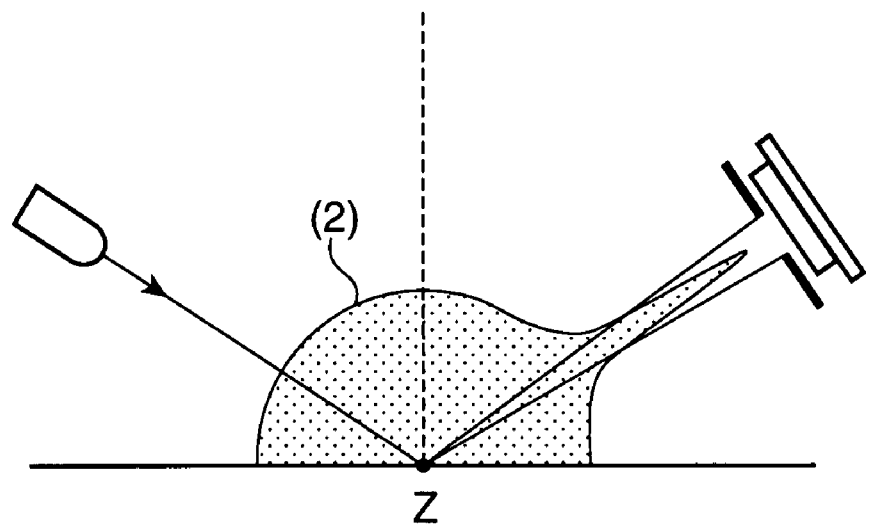

In the conventional example (e.g. see FIG. 10), the diaphragm 104 is disposed on the optical path between the lens element 107 corresponding to the third lens element 7, and the light detector 106 corresponding to the image sensor 8. In the conventional example, light to be directed to the light receiving surface of the light detector 106, which corresponds to the pixel area, from which pixel output values are obtained for calculation of the degree of gloss, i.e., the area W1 in FIG. 3, is mechanically defined, and the dimensions of the aperture of the diaphragm are fixed. In the conventional example, if the sample surface S is tilted, as shown in FIG. 6, light which is supposed to be incident onto the light receiving surface of the light detector 106 is not incident, and the amount of light to be directed to a pixel area E which is used in calculation of the degree of gloss is resultantly changed. In particular, if the tilting amount of the sample surface S is exceedingly large, the specular reflection light is not incident onto the pixel area E, which may lead to a failure that the output from the light detector 106 does not include a peak value corresponding to the peak position.

In view of the above, in the embodiment, in place of providing a diaphragm in the reflection-side optical system 2b, the trimming range determiner 19 extracts output values of the pixels belonging to the area substantially equal to the dimensions of the aperture of the diaphragm for trimming. By the trimming, the pixel area (hereinafter, called as "trimming range"), from which the pixel output values to be used in calculation of the degree of gloss are obtained, is electrically defined. Also, in the case where the peak position PK is detected by the peak position detector 18, the trimming range is changed depending on the peak position.

For instance, if the peak position PK shown in FIG. 5 is displaced to the peak position PK' shown in FIG. 6 due to a change in setting position of the sample surface S, the trimming range determiner 19 determines a pixel area F having substantially the same dimensions as those of the pixel area E, as a trimming range, with the peak position PK' being defined as the center of the pixel area F.

If, on the other hand, the peak position detector 18 detects that the output distribution profile does not include a peak value, in other words, the sample surface S has a relatively small degree of gloss, the trimming range determiner 19 determines the pixel area E, as a trimming range, with a pixel located at the center O (see FIG. 6) of the light receiving surface, as the first area, of the image sensor 8 being used as a reference pixel.

The reflection characteristic calculator 20 calculates the degree of gloss, using a predetermined computation formula, based on the sum of the output values of the pixels belonging to the trimming range determined by the trimming range determiner 19.

The display controller 21 controls the display section 13 to display the degree of gloss calculated by the reflection characteristic calculator 20.

Figure 7:
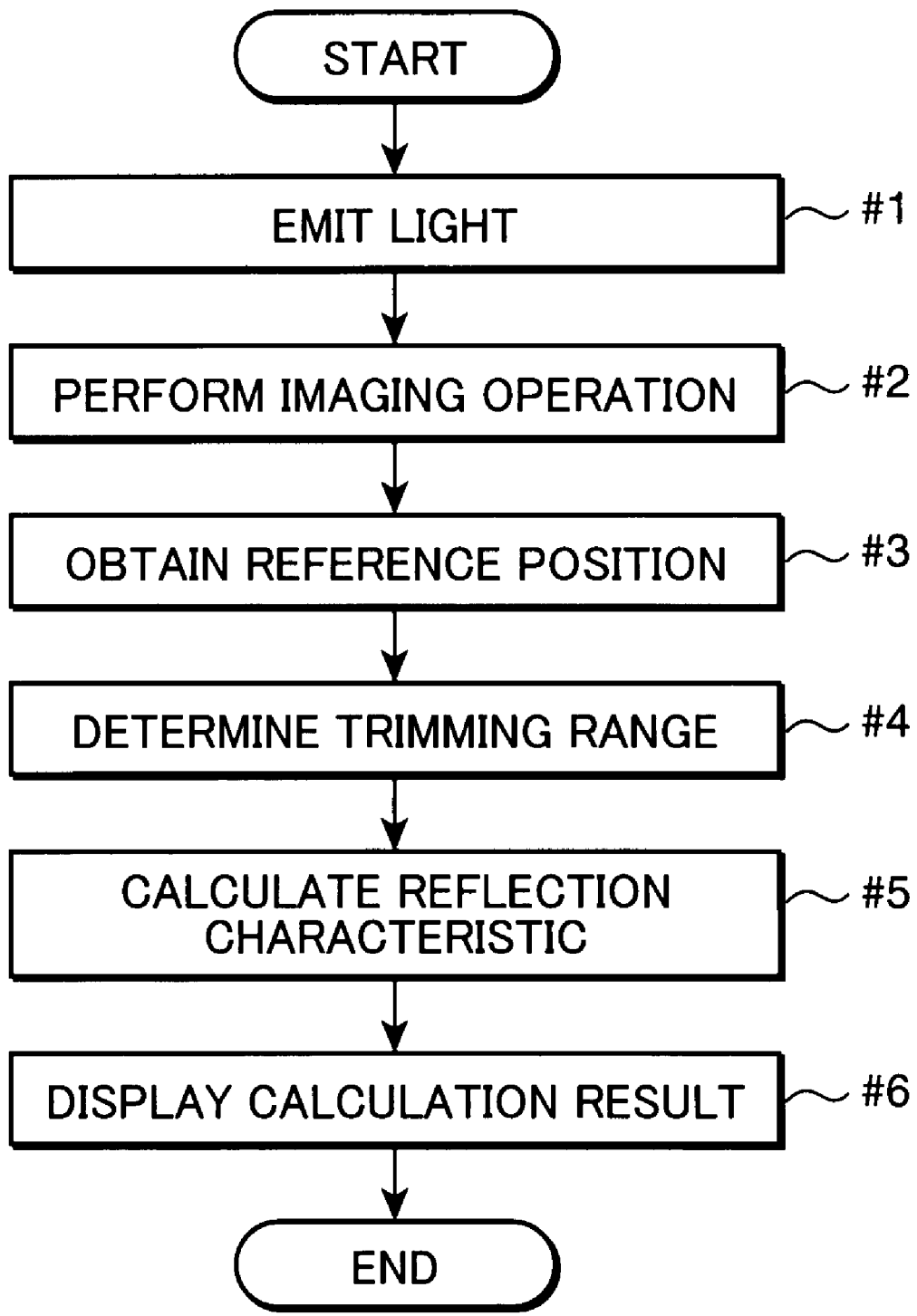
FIG. 7 is a flowchart showing a gloss measurement operation to be executed by the reflection characteristic measuring apparatus.

FIG. 7 is a flowchart showing a gloss measurement operation to be executed by the reflection characteristic measuring apparatus 1. First, the main controller 15 controls the light source 3 to emit light (Step #1), and controls the image sensor 8 to perform an imaging operation (Step #2). Then, the main controller 15 controls the peak position detector 18 to detect whether there exists a peak value among output values of the pixels of the image sensor 8 to obtain a reference position for determining the trimming range (Step #3). If it is detected that there exists the peak value, the position of the pixel which has outputted the peak value is defined as the reference position. If, on the other hand, it is detected that there does not exist the peak value, the position of the pixel located at the center O of the light receiving surface of the image sensor 8 is defined as the reference position. Then, the main controller 15 controls the trimming range determiner 19 to determine a predetermined area (e.g. the pixel area F shown in FIG. 6), as the trimming range, with the reference position determined in Step #3 being defined as the center of the trimming range (Step #4).

Thereafter, the main controller 15 controls the reflection characteristic calculator 20 to calculate a reflection characteristic i.e. the degree of gloss, based on the sum of the output values of the pixels belonging to the trimming range (Step #5). Then, the main controller 15 causes the display controller 21 to display the calculated reflection characteristic on the display section 13 (Step #6).

As mentioned above, in the reflection characteristic measuring apparatus 1 of the embodiment, unlike the conventional arrangement, in place of providing a diaphragm between the image sensor 8 and the third lens element 7, the pixels corresponding to the output values to be used in calculation of the degree of gloss are electrically defined by trimming the output values of the pixels belonging to the area having the dimensions substantially equal to the aperture diameter of the diaphragm, based on the output from the image sensor 8. Also, the pixel area to be used in calculation of the degree of gloss is changed i.e. shifted depending on the peak position. With this arrangement, even if the sample surface S is set in a tilted position, the degree of gloss can be calculated, based on output values substantially equal to the output values concerning the area having the peak position as a reference position in a condition that the setting position of the sample surface S is not changed. This enables to obtain an accurate degree of gloss of the sample surface S.

Also, detection is made as to whether there exists the peak value. If it is detected that there exists the peak value, the degree of gloss of the sample surface S is obtained, based on the output values of the pixels belonging to the aforementioned predetermined pixel area, with the peak position being defined as the reference position. The above arrangement is advantageous in maximally utilizing an output value corresponding to specular reflection light, as the output value to be used in obtaining the degree of gloss of the sample surface S, even if the setting position of the sample surface S is changed. With this arrangement, the characteristic of the sample surface S with a particularly large degree of gloss i.e. a large ratio of specular reflection light component can be accurately measured.

Also, in the case where it is detected that there does not exist the peak value, the predetermined pixel area, with the pixel at the center O (see FIG. 6) on the light receiving surface of the image sensor 8 being defined as the reference position, is determined as a trimming range. This arrangement enables to obtain the characteristic of the sample surface S in the case where the peak value is not detected.

Further, in the embodiment, the dimensions of the pixel area i.e. an angular range for obtaining the degree of gloss of the sample surface can be changed, in addition to the position of the pixel area to be used in calculation of the degree of gloss. With this arrangement, there can be confirmed that the sum of the output values of the pixels belonging to the pixel area is different concerning sample surfaces whose degree of gloss is identical, but whose ratio of specular reflection light component to diffusion light component is different i.e. reflection characteristic is different, by changing the dimensions of the pixel area for trimming. This enables to distinguish the sample surfaces having different reflection characteristics one from another.

The invention may include the following modifications (1) through (4) in addition to or in place of the foregoing embodiment.

(1) In the foregoing embodiment, the method for detecting the maximal output value i.e. the peak value among the pixel output values to define the position of the pixel which has outputted the peak value as the peak position is adopted as the method for detecting the peak position. Alternatively, the following method may be applied to detect the peak position.

Figure 8:
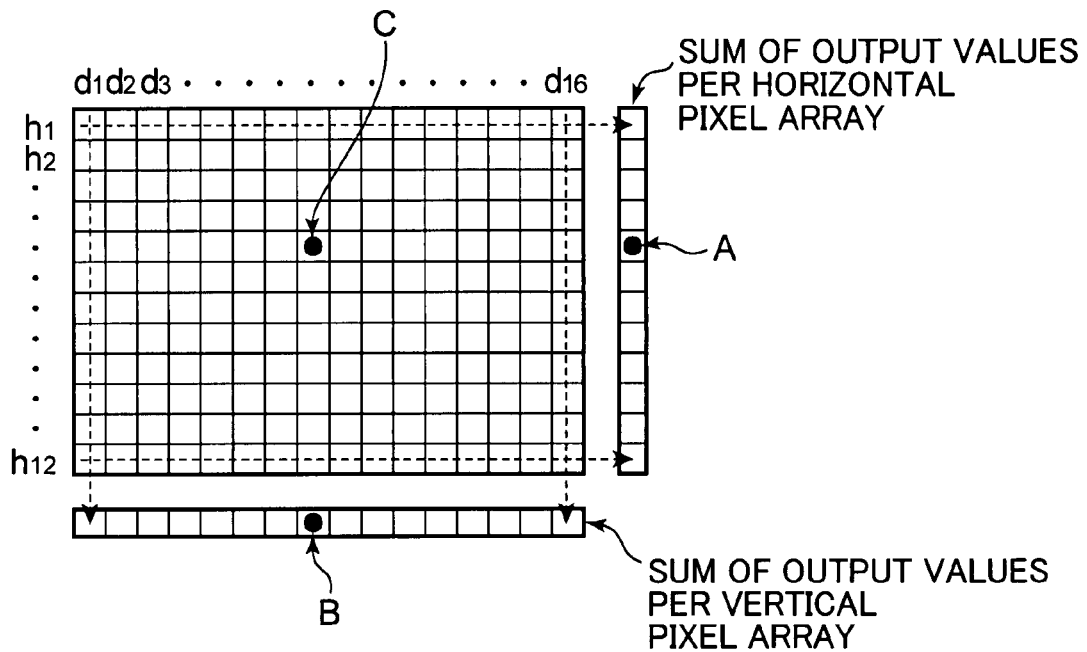
FIG. 8 is a diagram for describing an approach for detecting a peak position.

Specifically, as shown in FIG. 8, let it be assumed that the image sensor 8 is constituted of sixteen pixels in a row and twelve pixels in a column, wherein horizontal pixel arrays in a horizontal direction are expressed as h1, h2, 3, . . . , and h12, and vertical pixel arrays in a vertical direction are expressed as d1, d2, d3 . . . , and d16.

Then, the sum of the output values of the pixels belonging to each of the horizontal pixel arrays h1 to h12 is calculated to detect a maximal sum among the sums concerning the horizontal pixel arrays. Now, let it be assumed that, as shown by the arrow A in FIG. 7A, the sum of the output values of the pixels in the horizontal pixel array h5 is maximal among the sums concerning the horizontal pixel arrays. Likewise, the sum of the output values of the pixels belonging to each of the vertical pixel arrays d1 to d16 is calculated to detect a maximal sum among the sums concerning the vertical pixel arrays. Now, let it be assumed that, as shown by the arrow B in FIG. 8, the sum of the output values of the pixels in the vertical pixel array d8 is maximal among the sums concerning the vertical pixel arrays.

Then, the position of the pixel that belongs both to the horizontal pixel array whose sum of the output values of the pixels is judged to be maximal, and to the vertical pixel array whose sum of the output values of the pixels is judged to be maximal is defined as the peak position. For instance, in the example of FIG. 8, the position of the pixel indicated by the arrow C, which belongs both to the horizontal pixel array h5 and to the vertical pixel array d8 is obtained as the peak position.

The aforementioned detection method is advantageous, as compared with the method described in the embodiment, in eliminating the need of comparison among output values of multitudes of pixels, thereby contributing to shortening of the processing time required for obtaining the peak position.

Figure 9:
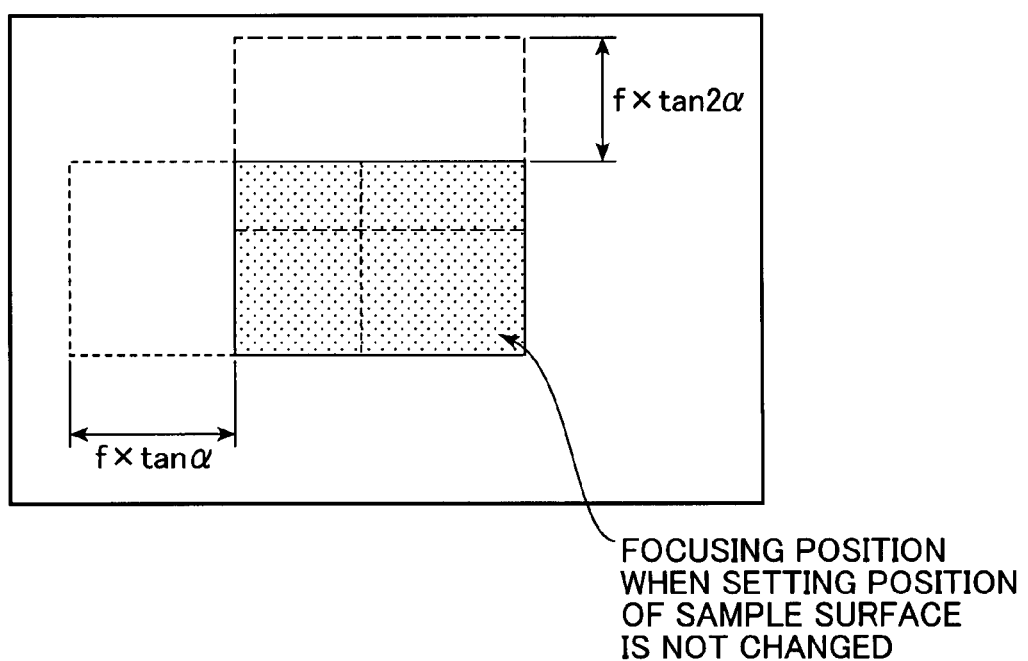
FIG. 9 is a diagram showing a second modified embodiment.

(2) In the foregoing embodiment, the trimming range to be used in calculation of the degree of gloss is shifted in the vertical direction. Alternatively, as shown in FIG. 9, the trimming range may be shifted in a horizontal direction, in addition to the vertical direction.

Specifically, assuming that a horizontal direction on the plane of FIG. 1 is defined as X-axis direction, and a direction orthogonal to the X-axis direction is defined as Y-axis direction, if the sample surface S is tilted by the angle α with respect to the X-axis direction, the direction of reflection light from the sample surface S is changed by the angle 2α, as compared with a condition that the setting position of the sample surface S is not changed. In such a condition, as shown in FIG. 9, the trimming range may be shifted in the vertical direction by f×tan 2α, because the focusing position of the reflection light on the light receiving surface of the image sensor 8 is shifted in the vertical direction by f×tan 2α.

Likewise, if the sample surface S is tilted by the angle α with respect to the Y-axis direction, the direction of reflection light from the sample surface S is changed by the angle α, as compared with a condition that the setting position of the sample surface S is not changed. In such a condition, as shown in FIG. 9, the trimming range may be shifted in the horizontal direction by f×tan α, because the focusing position of reflection light on the light receiving surface of the image sensor 8 is shifted in the horizontal direction by f×tan α.

(3) In the case where a load of a process of detecting the peak position is unduly large, or shortening of the processing time is required, it may be preferable to provide a dedicated IC of executing the process, in addition to the main controller 15.

(4) In the embodiment, the area sensor is used as the image sensor 8. Alternatively, a line sensor having a plurality of light receiving units arrayed in a line may be used. In the modification, an imaging operation is performed while moving the line sensor in a direction perpendicular to the pixel array direction to obtain two-dimensional light receiving data. Further alternatively, a spot-like sensor provided with a significantly small light receiving area may be used. In the latter modification, an imaging operation is performed while moving the sensor in two-dimensional directions to obtain two-dimensional light receiving data.

The foregoing embodiment and/or modifications primarily include the invention having the following arrangements.

A reflection characteristic measuring apparatus according to an aspect of the invention comprises: a light irradiating member for irradiating light toward a sample surface to be measured; a light detector, having a two-dimensional light receiving surface, for receiving reflection light from the sample surface illuminated with the light irradiated by the light irradiating member to output two-dimensional light receiving data concerning a first area corresponding to an area of the light receiving surface; an area setter for setting a second area at an appropriate position within the first area, the second area being smaller than the first area, to restrict light receiving data to be used in obtaining a reflection characteristic of the sample surface; and a calculator for obtaining a characteristic of the sample surface, based on two-dimensional light receiving data concerning the second area, wherein the area setter detects whether the two-dimensional light receiving data concerning the first area includes a peak value concerning light receiving, the area setter sets the second area, with a position of the peak value being defined as a reference position, if the peak value is detected, and the area setter sets the second area, with a central position of the first area being defined as the reference position, if the peak value is not detected.

In the above arrangement, the characteristic of the sample surface is obtained, based on the light receiving data concerning the second area among the two-dimensional light receiving data concerning the first area based on the output from the light detector. This arrangement enables to change the light receiving data to be used in obtaining the characteristic of the sample surface depending on the setting position of the sample surface.

Also, if the peak value is detected, the area setter sets the second area, with the position of the peak value being defined as the reference position. Then, the calculator obtains the characteristic of the sample surface based on the light receiving data concerning the second area. In this arrangement, even if the setting position of the sample surface is changed, the light receiving data corresponding to specular reflection light is included in the light receiving data to be used in obtaining the characteristic of the sample surface.

If, on the other hand, the peak value is not detected, the area setter sets the second area, with the central position on the light receiving surface of the light detector being defined as the reference position. Then, the calculator obtains the characteristic of the sample surface based on the light receiving data concerning the second area. This arrangement enables to obtain the characteristic of the sample surface in the case where the peak value is not detected.

In the above arrangement, even in a condition that the setting position of the sample surface is changed, the gloss of the sample surface can be accurately measured, while distinguishing a sample surface having a relatively large ratio of specular reflection light component to diffusion light component from a sample surface having a relatively small ratio of specular reflection light component to diffusion light component. In other words, this arrangement enables to accurately measure the characteristic of the sample surface with more gloss i.e. having a relatively large ratio of specular reflection light component, and also enables to measure the characteristic of the sample surface with such less gloss that the peak value is undetectable.

Preferably, the reflection characteristic measuring apparatus may further comprise an optical system for directing the reflection light from the sample surface toward the light receiving surface of the light detector, wherein the optical system is operable to allow specular reflection light from the sample surface set within a predetermined angular range to be incident onto the area of the light receiving surface of the light detector.

Further preferably, the light irradiating member may include a light source for emitting light, and a first optical system for directing the light emitted by the light source toward the sample surface, the apparatus may further comprise a second optical system for directing the reflection light from the sample surface toward the light receiving surface of the light detector, the first optical system may be an optical system having a first lens element and a diaphragm, the second optical system may be an optical system having a second lens element, the second optical system substantially excluding a diaphragm, the diaphragm and the light receiving surface of the light detector may be positioned in optically conjugated relations with each other, and the second lens element may have such a focal length that specular reflection light from the sample surface set within a predetermined angular range is allowed to be incident onto the area of the light receiving surface of the light detector.

In the above arrangements, the reflection characteristic of the sample surface set within the predetermined angular range can be accurately obtained, without providing a diaphragm in the second optical system to direct the reflection light from the sample surface toward the light receiving surface of the light detector.

Preferably, the light detector may include an area sensor having pixels arrayed in a matrix.

The above arrangement enables to eliminate a scanning operation, unlike an arrangement in which a point sensor having a spot-like light receiving area is moved to scan in two-dimensional directions so as to obtain two-dimensional light receiving data, or an arrangement in which a line sensor with linearly-arranged pixels is moved to scan in a direction orthogonal to the pixel array direction so as to obtain two-dimensional light receiving data. Accordingly, the arrangement is advantageous in avoiding cost increase and size increase concerning the apparatus.

In the above arrangement, preferably, the calculator may execute the following first to third processes:

the first process of calculating the sum of light receiving data concerning each of horizontal pixel arrays in a horizontal direction of the area sensor to determine a horizontal pixel array having a maximal sum among the sums concerning the horizontal pixel arrays;

the second process of calculating the sum of light receiving data concerning each of vertical pixel arrays in a vertical direction of the area sensor to determine a vertical pixel array having a maximal sum among the sums concerning the vertical pixel arrays; and the third process of setting the position of a pixel that belongs both to the horizontal pixel array having the maximal sum obtained in the first process, and to the vertical pixel array having the maximal sum obtained in the second process, as a position of the peak value.

In the above arrangement, as compared with a method for comparing pixel output values from the light detector one from another to detect the maximal output value, the position of the peak value can be detected in a simplified manner. This enables to simplify a program or a circuit for realizing the peak position detection.

In the above arrangements, preferably, the characteristic of the sample surface may be a characteristic concerning gloss of the sample surface. This arrangement is advantageous in obtaining the reflection characteristic measuring apparatus for measuring the characteristic concerning gloss of the sample surface having the aforementioned advantages.

A reflection characteristic measuring apparatus according to another aspect of the invention comprises: a light irradiating member for irradiating light toward a sample surface to be measured; a light detector, having a two-dimensional light receiving surface, for receiving reflection light from the sample surface illuminated with the light irradiated by the light irradiating member to output two-dimensional light receiving data concerning a first area corresponding to an area of the light receiving surface; an optical system for directing the reflection light from the sample surface toward the light receiving surface of the light detector; an area setter for setting a second area at an appropriate position within the first area, the second area being smaller than the first area, to restrict light receiving data to be used in obtaining a reflection characteristic of the sample surface; and a calculator for obtaining a characteristic of the sample surface, based on two-dimensional light receiving data concerning the second area, wherein the optical system is operable to allow specular reflection light from the sample surface set within a predetermined angular range to be incident onto the area of the light receiving surface of the light detector, and the area setter sets the second area based on an incident position of the specular reflection light onto the light receiving surface of the light detector.

A reflection characteristic measuring apparatus according to yet another aspect of the invention comprises: a light source for emitting light; a first optical system for directing the light emitted by the light source toward a sample surface to be measured; a light detector, having a two-dimensional light receiving surface, for receiving reflection light from the sample surface illuminated with the light emitted by the light source to output two-dimensional light receiving data concerning a first area corresponding to an area of the light receiving surface; a second optical system for directing the reflection light from the sample surface toward the light receiving surface of the light detector; an area setter for setting a second area at an appropriate position within the first area, the second area being smaller than the first area, to restrict light receiving data to be used in obtaining a reflection characteristic of the sample surface; and a calculator for obtaining a characteristic of the sample surface, based on two-dimensional light receiving data concerning the second area, wherein the first optical system is an optical system having a first lens element and a diaphragm, the second optical system is an optical system having a second lens element, the second optical system substantially excluding a diaphragm, the diaphragm and the light receiving surface of the light detector are positioned in optically conjugated relations with each other, the second lens element has such a focal length that specular reflection light from the sample surface set within a predetermined angular range is allowed to be incident onto the area of the light receiving surface, and the area setter sets the second area based on an incident position of the specular reflection light onto the light receiving surface.

A reflection characteristic measuring apparatus according to still another aspect of the invention comprises: a light irradiating member for irradiating light toward a sample surface; a light detector, having a plurality of light receiving units arrayed in a line, for receiving reflection light from the sample surface illuminated with the light to output data relating to the plurality of light receiving units; an area setter for setting a specific area being smaller than an area of the plurality of light receiving units to restrict light receiving data to be used in obtaining a reflection characteristic of the sample surface; and a calculator for obtaining a characteristic of the sample surface, based on the data relating to the plurality of light receiving units concerning the specific area, wherein the area setter detects whether the data relating to the plurality of light receiving units includes a peak value concerning light receiving, the area setter sets the specific area, with a position of the peak value being defined as a reference position if the peak value is detected, and the area setter sets the specific area, with a central position on the area of the plurality of light receiving units being defined as a reference position, if the peak value is not detected.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. A reflection characteristic measuring apparatus, comprising:

a light irradiating member for irradiating light toward a sample surface to be measured;

a light detector, having a two-dimensional light receiving surface, for receiving reflection light from the sample surface illuminated with the light irradiated by the light irradiating member to output two-dimensional light receiving data concerning a first area corresponding to an area of the light receiving surface;

an area setter for setting a second area at an appropriate position within the first area, the second area being smaller than the first area, to restrict light receiving data to be used in obtaining a reflection characteristic of the sample surface; and a calculator for obtaining a characteristic of the sample surface, based on two-dimensional light receiving data concerning the second area, wherein the area setter detects whether the two-dimensional light receiving data concerning the first area includes a peak value concerning light receiving, the area setter sets the second area, with a position of the peak value being defined as a reference position, if the peak value is detected, and the area setter sets the second area, with a central position on the first area being defined as the reference position, if the peak value is not detected.

2. The reflection characteristic measuring apparatus according to claim 1, further comprising:

an optical system for directing the reflection light from the sample surface toward the light receiving surface of the light detector, wherein the optical system is operable to allow specular reflection light from the sample surface set within a predetermined angular range to be incident onto the area of the light receiving surface of the light detector.

3. The reflection characteristic measuring apparatus according to claim 1, wherein the light irradiating member includes a light source for emitting light, and a first optical system for directing the light emitted by the light source toward the sample surface, the apparatus further comprises a second optical system for directing the reflection light from the sample surface toward the light receiving surface of the light detector, the first optical system is an optical system having a first lens element and a diaphragm, the second optical system is an optical system having a second lens element, the second optical system substantially excluding a diaphragm, the diaphragm and the light receiving surface of the light detector are positioned in optically conjugated relations with each other, and the second lens element has such a focal length that specular reflection light from the sample surface set within a predetermined angular range is allowed to be incident onto the area of the light receiving surface of the light detector.

4. The reflection characteristic measuring apparatus according to claim 1, wherein the light detector includes an area sensor having pixels arrayed in a matrix.

5. The reflection characteristic measuring apparatus according to claim 4, wherein the calculator executes the following first to third processes:

the first process of calculating the sum of light receiving data concerning each of horizontal pixel arrays in a horizontal direction of the area sensor to determine a horizontal pixel array having a maximal sum among the sums concerning the horizontal pixel arrays;

the second process of calculating the sum of light receiving data concerning each of vertical pixel arrays in a vertical direction of the area sensor to determine a vertical pixel array having a maximal sum among the sums concerning the vertical pixel arrays; and the third process of setting the position of a pixel that belongs both to the horizontal pixel array having the maximal sum obtained in the first process, and to the vertical pixel array having the maximal sum obtained in the second process, as a position of the peak value.

6. The reflection characteristic measuring apparatus according to claim 1, wherein the characteristic of the sample surface is a characteristic concerning gloss of the sample surface.

7. A reflection characteristic measuring apparatus, comprising:

a light irradiating member for irradiating light toward a sample surface to be measured;

a light detector, having a two-dimensional light receiving surface, for receiving reflection light from the sample surface illuminated with the light irradiated by the light irradiating member to output two-dimensional light receiving data concerning a first area corresponding to an area of the light receiving surface;

an optical system for directing the reflection light from the sample surface toward the light receiving surface of the light detector;

an area setter for setting a second area at an appropriate position within the first area, the second area being smaller than the first area, to restrict light receiving data to be used in obtaining a reflection characteristic of the sample surface; and a calculator for obtaining a characteristic of the sample surface, based on two-dimensional light receiving data concerning the second area, wherein the optical system is operable to allow specular reflection light from the sample surface set within a predetermined angular range to be incident onto the area of the light receiving surface of the light detector, and the area setter sets the second area based on an incident position of the specular reflection light onto the light receiving surface of the light detector.

8. A reflection characteristic measuring apparatus, comprising:

a light source for emitting light;

a first optical system for directing the light emitted by the light source toward a sample surface to be measured;

a light detector, having a two-dimensional light receiving surface, for receiving reflection light from the sample surface illuminated with the light emitted by the light source to output two-dimensional light receiving data concerning a first area corresponding to an area of the light receiving surface;

a second optical system for directing the reflection light from the sample surface toward the light receiving surface of the light detector;

an area setter for setting a second area at an appropriate position within the first area, the second area being smaller than the first area, to restrict light receiving data to be used in obtaining a reflection characteristic of the sample surface; and a calculator for obtaining a characteristic of the sample surface, based on two-dimensional light receiving data concerning the second area, wherein the first optical system is an optical system having a first lens element and a diaphragm, the second optical system is an optical system having a second lens element, the second optical system substantially excluding a diaphragm, the diaphragm and the light receiving surface of the light detector are positioned in optically conjugated relations with each other, the second lens element has such a focal length that specular reflection light from the sample surface set within a predetermined angular range is allowed to be incident onto the area of the light receiving surface, and the area setter sets the second area based on an incident position of the specular reflection light onto the light receiving surface.

9. A reflection characteristic measuring apparatus, comprising:

a light irradiating member for irradiating light toward a sample surface;

a light detector, having a plurality of light receiving units arrayed in a line, for receiving reflection light from the sample surface illuminated with the light to output data relating to the plurality of light receiving units;

an area setter for setting a specific area being smaller than an area of the plurality of light receiving units to restrict light receiving data to be used in obtaining a reflection characteristic of the sample surface; and a calculator for obtaining a characteristic of the sample surface, based on the data relating to the plurality of light receiving units concerning the specific area, wherein the area setter detects whether the data relating to the plurality of light receiving units includes a peak value concerning light receiving, the area setter sets the specific area, with a position of the peak value being defined as a reference position if the peak value is detected, and the area setter sets the specific area, with a central position on the area of the plurality of light receiving units being defined as a reference position, if the peak value is not detected.

* * * * *